United States Patent [19]

de Fraine et al.

[11] 4,394,151
[45] Jul. 19, 1983

[54] AZOLYL-HYDROXY ALKANOIC ACID COMPOUNDS

[75] Inventors: Paul de Fraine, Wokingham; John M. Clough, High Wycombe; Paul A. Worthington, Maidenhead, all of England

[73] Assignee: Imperial Chemical Industries PLC, London, England

[21] Appl. No.: 288,203

[22] Filed: Jul. 29, 1981

[30] Foreign Application Priority Data

Aug. 22, 1980 [GB] United Kingdom ............... 8027451

[51] Int. Cl.³ .................... A01N 43/50; A01N 43/64; C07D 233/60; C07D 249/08
[52] U.S. Cl. .......................................... 71/76; 71/92; 424/245; 424/269; 424/273 R; 548/101; 548/269; 548/336; 548/341
[58] Field of Search ............. 548/101, 262, 341, 336; 424/245, 269, 273 R; 71/76, 92

[56] References Cited

U.S. PATENT DOCUMENTS

| 3,843,667 | 10/1974 | Cupery | 548/341 |
| 4,289,526 | 9/1981 | Worthington et al. | 548/336 |
| 4,331,674 | 5/1982 | Kramer et al. | 548/341 |
| 4,351,839 | 9/1982 | Chan | 548/262 |

FOREIGN PATENT DOCUMENTS

| 2654890 | 6/1977 | Fed. Rep. of Germany | 548/262 |
| 1563199 | 3/1980 | United Kingdom | 548/262 |

OTHER PUBLICATIONS

Wagner et al., Synthetic Organic Chemistry, (New York, 1953), p. 177.

Primary Examiner—Alton D. Rollins
Attorney, Agent, or Firm—Cushman, Darby & Cushman

[57] ABSTRACT

Compounds of formula

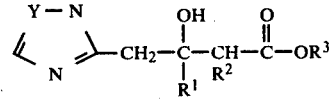

useful as fungicides and plant growth regulators.

7 Claims, No Drawings

AZOLYL-HYDROXY ALKANOIC ACID COMPOUNDS

This invention relates to triazole and imidazole compounds useful as fungicides and plant growth regulators, to a process for preparing them, to fungicidal and plant growth regulating compositions containing them, and to methods of using them to combat fungal infections in plants and to regulate plant growth.

The invention provides a racemic compound having the general formula (I):

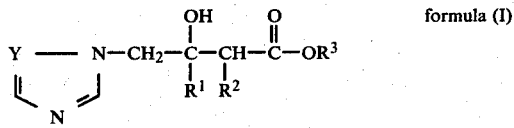

and stereoisomers thereof, wherein Y is —CH= or =N—, $R^1$ is alkyl, cycloalkyl or optionally substituted phenyl and $R^2$ and $R^3$, which may be the same or different, are hydrogen, alkyl, cycloalkyl, (e.g. cyclopropyl, cyclopentyl or cyclohexyl), optionally substituted phenyl or optionally substituted benzyl, or together form a lactone ring; and acid addition salts, ethers, esters and metal complexes thereof.

The compounds of the invention can contain chiral centres. Such compounds are generally obtained in the form of racemic mixtures. However, these and other mixtures can be separated into the individual isomers by methods known in the art and this invention embraces such isomers.

The alkyl groups can be a straight or branched chain group having 1 to 6, e.g. 1 to 4, carbon atoms; examples are methyl, ethyl, propyl (n- or iso-propyl) and butyl (n-, sec-, iso- or t-butyl).

Examples of suitable substituents for the phenyl and for the phenyl moiety of the benzyl are halogen, alkyl, alkoxy, nitro and phenyl. The alkyl moiety of the benzyl can be substituted with for example one alkyl (e.g. methyl or ethyl). Suitably the phenyl and benzyl are unsubstituted or substituted with 1, 2 or 3 ring substituents as defined above. Examples of these groups are phenyl, benzyl, α-methylbenzyl, 2-, 3- or 4-chlorophenyl, 2,4- or 2,6-dichlorophenyl, 2-, 3- or 4-fluorophenyl, 2-, 3- or 4-bromophenyl, 2-, 3- or 4-methoxyphenyl, 2,4-dimethoxyphenyl, 2-, 3- or 4-ethoxyphenyl, 2-, 3- or 4-nitrophenyl, 2-, 3- or 4- methylphenyl, 2-, 3- or 4-trifluoromethylphenyl), and 4-phenylphenyl (4-biphenylyl), and the corresponding ring substituted benzyl and α-methylbenzyl groups.

In a further aspect, therefore, the invention provides a racemic compound of formula (I) above, or a stereoisomer thereof, wherein $R^1$ is a straight or branched chain alkyl group having from 1 to 6 carbon atoms or is phenyl optionally substituted with halogen, alkyl, alkoxy, nitro, phenyl or phenoxy; $R^2$ and $R^3$ are together an alkylene bridging group, or each represents hydrogen, straight or branched chain alkyl groups having from 1 to 6 carbon atoms, phenyl or benzyl each optionally substituted with halogen, alkyl, alkoxy, nitro, phenyl or phenoxy, the alkyl moiety of the benzyl being optionally substituted with alkyl; and Y is =CH— or =N—.

In a preferred aspect the invention provides a compound of formula (I) above, or a stereoisomer thereof, wherein $R^1$ is an alkyl group containing from 1 to 4 carbon atoms or is halophenyl, $R^2$ is hydrogen or methyl; $R^3$ is an alkyl group containing from 1 to 4 carbon atoms and Y is =N— or =CH—.

The salts can be salts with inorganic or organic acids e.g. hydrochloric, nitric, sulphuric, acetic, 4-toluenesulphonic or oxalic acid. The esters are suitably alkanoates (e.g. acetates) and the ethers are suitably alkyl (e.g. methyl or ethyl), aryl (e.g. phenyl) or aralkyl (e.g. benzyl) ethers.

Suitably the metal complex is one including, as the metal, copper, zinc, manganese or iron. It preferably has the general formula:

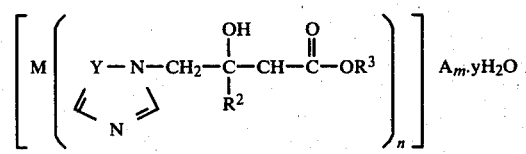

wherein Y, $R^1$, $R^2$ and $R^3$ are as defined above, M is a metal, A is an anion (e.g. a chloride, bromide, iodide, nitrate, sulphate or phosphate anion), n is 2 or 4, y is 0 or an integer of 1 to 12, and m is an integer consistent with valency.

Examples of the compounds of the invention are shown in Table 1. These conform to formula I.

TABLE 1

| COMPOUND NO | $R^1$ | $R^2$ | $R^3$ | Y | MELTING POINT (°C.) |
|---|---|---|---|---|---|
| 1 | 4-chlorophenyl | H | ethyl | =N— | 84 |
| 2 | 4-chlorophenyl | H | tertiary butyl | =N— | 94–6 |
| 3 | 4-fluorophenyl | H | tertiary butyl | =N— | 92–4 |
| 4 | 4-chlorophenyl | *—CH$_2$—CH$_2$— | | =N— | 163–4 |
| 5 | tertiary butyl | H | tertiary butyl | =N— | 140 |
| 6 | 2,4-dichlorophenyl | H | tertiary butyl | =N— | 137–9 |
| 7 | 2,4-dichlorophenyl | H | normal butyl | =N— | |
| 8 | 2,4-dichlorophenyl | H | tertiary butyl | =CH— | |
| 9 | 2,4-dichlorophenyl | CH$_3$ | tertiary butyl | =N— | |
| 10 | 2,4-dichlorophenyl | CH$_3$ | tertiary butyl | =CH— | |
| 11 | 4-chlorophenyl | CH$_3$ | tertiary butyl | =N— | |
| 12 | 4-chlorophenyl | CH$_3$ | tertiary butyl | =CH— | |
| 13 | 4-(4-chlorophenyl)phenyl | H | tertiary butyl | =N— | |
| 14 | 4-(4-chlorophenyl)phenyl | H | tertiary butyl | =CH— | |

*i.e. $R^2$ and $R^3$ together form a bridging group

The compounds of general formula (I) may be produced by reacting a compound of general formula (II) with (III) in a Reformatsky reaction using zinc dust or a zinc-copper couple.

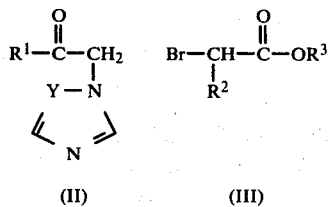

(II)    (III)

The compounds of general formula (II) and (III) may be made by methods set out in the literature.

Suitably the compounds of general formula (II) and (III) are refluxed in a convenient solvent such as THF with zinc powder. The product can be isolated by pouring the reaction mixture into water and recrystallising the solid formed from a convenient solvent.

The salts, ethers, esters and metal complex of the compounds of general formula (I) can be prepared from the latter in known manner. For example, the complexes can be made by reacting the uncomplexed compound with a metal salt in a suitable solvent.

The compounds, salts and metal complexes are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Helminthosporium* spp. and *Rhynchosphorium* spp. on cereals

*Cercospora arachidicola* on peanuts and other Cercospora species on for example sugar beet, bananas and soya beans

*Botrytis cinerea* (grey mould) on tomatoes, strawberries, vines and other hosts

*Phytophthora infestans* (late blight) on tomatoes

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., Helminthosporium spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

The compounds, and their derivatives as defined above, also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals and soya bean where reduction in stem growth may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata*, *Festuca* spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in for example grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape fruit trees (e.g. apples). Some coniferous trees are not significantly stunted by the compounds so the compounds could be useful in controlling undesirable vegetation in conifer nurseries.

The plant growth regulating effect may (as implied) above) manifest itself in an increase in crop yield.

In the potato, vine control in the field and inhibition of sprouting in the store may be possible.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. In grass swards an increase in tillering could lead to a denser sward which may result in increased resilience in wear.

The treatment of plants with the compounds can lead to the leaves developing a darker green colour.

The compounds may inhibit, or at least delay, the flowering of sugar beet and thereby may increase sugar yield. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus further provides a fungicidal or plant growth regulating composition comprising a compound of general formula (I) as hereinbefore defined, or a salt, metal complex, ether or ester thereof; and, optionally, a carrier or diluent.

The invention also provides a method of combating fungi, which comprises applying to a plant, to seed of a plant or to the locus of a plant or seed, a compound, or salt, metal complex, ether or ester thereof, as hereinbefore defined.

The invention also provides a method of regulating plant growth which comprises applying to a plant, to seed of a plant or to the locus of a plant or seed, a compound, or salt, metal complex, ether or ester thereof, as hereinbefore defined.

The compounds, salts, metal complexes, ethers and esters can be applied in a number of ways, for example they can be formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and puspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-anionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogenous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylene-sulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or plant growth regulating activity or compounds having herbicidal or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, dimethirimol, bupirimate, chlorothalonil, vinclozolin, procymidone, iprodione, metalaxyl, fosetyl-aluminium, carboxin, oxycarboxin, fenarimol, nuarimol, fenfuram, methfuroxam, nitrotal-isopropyl, triadimefon, thiabendazole, etridiazole, triadimenol, biloxazol, dithianon, binapacryl, quinomethionate, guazatine, dodine, fentin acetate, fentin hydroxide, dinocap, folpet, diclofluanid, ditalimphos, kitazin, fenpropemorph, cycloheximide, dichlorobutrazol, a dithiocarbamate, a copper compound, a mercury compound, DPX 3217, RH 2161, Chevron RE 20615, CGA 64250, CGA 54251 and RO 14-3169.

The compounds of general formula (I) can be mixed with soil, peat and other rooting media for the protection of plants against seed-borne, soil-borne or foliar fungal diseases.

Suitable insecticides are Pirimor, Croneton, dimethoate, Metasystox and formothion.

Examples of suitable plant growth regulating compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or BAP), phenoxyacetic acids (e.g. 2,4-D or MCPA), substituted benzoic acids (e.g. TIBA), morphactins (e.g. chlorfluorecol), maleic hydrazide, glyphosate, glyphosine, long chain fatty alcohols and acids (e.g. Off Shoot O or Off Shoot T), dikegulac, Sustar, Embark, substituted quaternary ammonium and phosphonium compounds (e.g. CCC or Phosfon-D), Ethrel, carbetamide, Racuza, Alar, asulam, abscissic acid, isopyrimol, RH531, hydroxybenzonitriles (e.g. bromoxynil), Avenge, Suffix or Lontrel.

The following Examples illustrates the invention; the temperatures are given in degrees Centigrade (°C.).

EXAMPLE 1 t-Butyl 3-(4-fluorophenyl)-3-hydroxy-4-(1,2,4-triazol-1-yl)butyrate (Compound 3)

2'-(1,2,4-Triazol-1-yl)-4-fluoroacetophenone (0.02 mol) and t-butyl bromoacetate (3.3 ml) were refluxed with zinc powder (2.5 g) in anhydrous tetrahydrofuran (60 ml) for 12 hours. The reaction mixture was poured into water and acidified with 2 N $H_2SO_4$. After extracting with ether (3×150 ml) and drying over anhydrous sodium sulphate, removal of the solvent gave a yellow solid which was recrystallised from (60–80) petroleum ether to give the title compound (40%) as a white crystalline solid m.p. 92°–4°.

EXAMPLE 2

2-[1-(4-chlorophenyl)-1-hydroxy-2-(1,2,4-triazol-1-yl)ethyl]butyrolactone (Compound 4)

2'-(1,2,4-Triazol-1-yl)-4-chloroacetophenone (0.02 mol) and 2-bromo-butyrolactone (1.8 ml) were refluxed with zinc powder (2.5 g) in tetrahydrofuran (60 ml) for 8 hours. The reaction mixture was poured into water and acidified with 2 N $H_2SO_4$. After extracting with chloroform (200 ml) the solution was washed with water (3×150 ml) and dried over anhydrous magnesium sulphate. Removal of the solvent gave an oil which on trituration with ethanol/petroleum ether (60–80) gave a white crystalline solid. Recrystallisation from ethanol gave the title compound (20%) as a white crystalline solid m.p. 163°–4°.

EXAMPLE 3 t-Butyl 3-(2,4-dichlorophenyl)-3-hydroxy-4-(1,2,4-triazol-1-yl)butyrate (Compound 6)

2'-(1,2,4-Triazol-1-yl)-2,4-dichloroacetophenone (0.02 mol) and t-butyl bromoacetate (4.0 ml) were refluxed with a zinc/copper couple (2.0 g) in tetrahydrofuran (100 ml) and ether (50 ml) for 24 hours. The reaction mixture was poured into water (200 ml) containing 2 N $H_2SO_4$ (50 ml), extracted with diethyl ether (3×300 ml), washed with brine, and dried over anhydrous magnesium sulphate. Removal of the solvent gave an oil which was purified by column chromatography on silica gel (K.6) eluted with ethyl acetate/petroleum ether 60/80 1:1 to give the title compound (20%) as a white crystalline solid m.p. 137°–9°.

EXAMPLE 4

The compounds were tested against a variety of foliar fungal diseases of plants. The technique employed was as follows.

The plants were grown in John Innes Potting Compost (No. 1 or 2) in 4 cm diameter minipots. A layer of fine sand was placed at the bottom of the pots containing the dicotyledonous plants to facilitate uptake of test compound by the roots. The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea*, *Plasmopara viticola* and *Venturia inaequalis*. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following gradinng:
- 4 = no disease
- 3 = trace-5% of disease on untreated plants
- 2 = 6-25% of disease on untreated plants
- 1 = 26-59% of disease on untreated plants
- 0 = 60-100% of disease on untreated plants The results are shown in Table II.

TABLE 2

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
|---|---|---|---|---|---|---|---|---|
| 1 | 4 | 4 | — | 0 | 0 | 2 | 3 | 4 |
| 2 | 4 | 4 | — | 2 | 0 | 0 | 4 | 4 |
| 3 | 4 | 4 | — | 1 | 0 | 3 | 4 | 3 |
| 4 | 4 | 4 | — | 0 | 0 | 1 | 4 | 4 |
| 5 | 4 | 4 | — | 0 | 0 | 2 | 3 | 1 |
| 6 | 4 | 4 | — | 0 | 0 | 4* | 4 | 4 |

"—" means not tested
*grape instead of tomato

EXAMPLE 5

This Example illustrates the plant growth regulating properties of the compounds. The compounds were applied in the form of a 4000 ppm solution in distilled water and the solution was then applied to the foliage of young seedlings of various plants. The experiments were replicated twice. After 12 or 13 days from treatment the plants were assessed for plant growth regulating effects and phytotoxic symptoms.

Table 3 shows the stunting effect of the compounds on the vegetative growth using the following grading:
- 1 = 0-30% retardation
- 2 = 31-75% retardation
- 3-75% retardation If no figure is given, the compound was substantially inactive as a stunting agent. Additional plant growth regulating properties are indicated as follows:
- G = darker green leaf colour
- A = apical effect
- T = side shooting effect

TABLE 3

| COMPOUND NUMBER | SOYA | COTTON | SUGAR BEET | AGROSTIS TENUIS | CYNOSURUS CRISTATUS | DACTYLIS GLOMERATA | WHEAT | LETTUCE | MAIZE | TOMATO |
|---|---|---|---|---|---|---|---|---|---|---|
| 2 | 1GA | 2G | 3GA | 3G | 3G | 1G | 1 | 3GA | — | 2GA |
| 3 | 2GA | 1G | 2GA | 3 | 2 | — | — | 2GAT | 2G | 2GA |

We claim:

1. A racemic compound having the general formula (I):

$$Y-N-CH_2-\underset{\underset{R^1}{|}}{\overset{\overset{OH}{|}}{C}}-\underset{\underset{R^2}{|}}{CH}-\overset{\overset{O}{\|}}{C}-OR^3$$

and stereoisomers thereof, wherein $R^1$ is a straight or branched chain alkyl group having from 1 to 6 carbons, phenyl or phenyl substituted with halogen, alkyl, alkoxy, nitro, phenyl or phenoxy; $R^2$ and $R^3$ are together a —$CH_2$—$CH_2$— bridging group, or each represents hydrogen, straight or branched chain alkyl groups having from 1 to 6 carbon atoms, phenyl or benzyl or phenyl or benzyl substituted with halogen, alkyl or alkoxy of 1 to 6 carbons, nitro, phenyl or phenoxy, the alkyl moiety of the benzyl being unsubstituted or substituted with alkyl of from 1 to 6 carbons; and Y is =N— or =CH—, and acid addition salts, alkyl, aralkyl or aryl ethers, alkanoate esters and metal complexes thereof.

2. A compound according to claim 1 of general formula (I), and stereoisomers thereof, wherein $R^1$ is an alkyl group containing from 1 to 4 carbon atoms or is halophenyl, $R^2$ is hydrogen or methyl; $R^3$ is an alkyl group containing from 1 to 4 carbon atoms; and Y is =N—.

3. A compound according to claim 1 wherein $R^1$ is phenyl, benzyl, α-methylbenzyl, 2-, 3- or 4-chloro-phenyl, 2,4- or 2,6-dichlorophenyl, 2-, 3- or 4-fluoro-phenyl, 2-, 3- or 4-bromophenyl, 2-, 3- or 4-methoxyphenyl, 2,4-dimethoxyphenyl, 2-, 3- or 4-ethoxy-phenyl, 2-, 3- or 4-nitrophenyl, 2-, 3- or 4-methylphenyl, 2-, 3- or 4-trifluoromethylphenyl, and 4-phenyl-phenyl, or is a correspondingly ring-substituted benzyl or α-methylbenzyl group; and Y is =N— or =CH—.

4. The racemic compound having the structure:

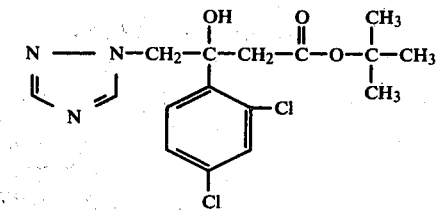

and its stereoisomers.

5. A fungicidal composition comprising as an active ingredient a fungicidally effective amount of a compound as defined in claim 1; or the indicated salt, ether, ester or metal complex thereof; and a carrier or diluent for the active ingredient.

6. A method of combating fungal diseases in a plant, which comprises applying to the plant, to seed of the plant, or to the locus of the plant or seed, a fungicidally effective amount of a compound as defined in claim 1.

7. A method of regulating plant growth which comprises applying to the plant, to seed of the plant, or to the locus of the plant or seed, a plant growth regulating amount of a compound as defined in claim 1.

* * * * *

UNITED STATES PATENT AND TRADEMARK OFFICE
CERTIFICATE OF CORRECTION

PATENT NO. : 4,394,151
DATED : July 19, 1983
INVENTOR(S) : Paul deFraine; John M. Clough, Paul A. Worthington It is certified that error appears in the above-identified patent and that said Letters Patent is hereby corrected as shown below:

In the ABSTRACT, the formula should read:

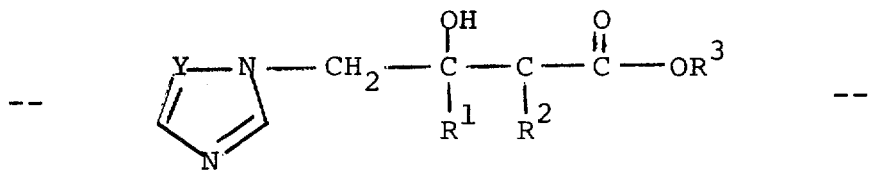

Column 2, the structural formula should read:

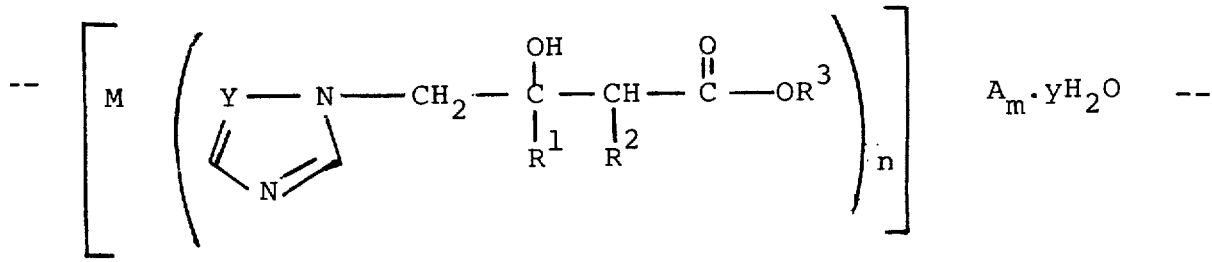

Signed and Sealed this

First Day of October 1985

[SEAL]

Attest:

DONALD J. QUIGG

Attesting Officer

Commissioner of Patents and
Trademarks—Designate